(12) United States Patent
Dekeyser et al.

(10) Patent No.: US 7,446,119 B2
(45) Date of Patent: Nov. 4, 2008

(54) MITICIDAL TRIAZOLIDINE DERIVATIVES

(75) Inventors: Mark A. Dekeyser, Waterloo (CA);
Paul T. McDonald, Middlebury, CT (US)

(73) Assignee: Crompton Corporation, Middlebury, CT (US)

( * ) Notice: Subject to any disclaimer, the term of this patent is extended or adjusted under 35 U.S.C. 154(b) by 478 days.

(21) Appl. No.: 11/092,493

(22) Filed: Mar. 28, 2005

(65) Prior Publication Data

US 2006/0217559 A1    Sep. 28, 2006

(51) Int. Cl.
*C07D 249/08* (2006.01)
*A01N 43/653* (2006.01)
(52) U.S. Cl. .................. 514/383; 548/262.2; 548/267.8; 548/268.6; 546/268.1; 546/272.4
(58) Field of Classification Search ............. 548/262.2, 548/627.8, 268.6; 514/383; 541/268.1, 272.4
See application file for complete search history.

(56) References Cited

U.S. PATENT DOCUMENTS

| 2,547,724 | A |   | 4/1951  | Sundholm |
| 3,621,099 | A | * | 11/1971 | Jacobson et al. ......... 548/263.4 |
| 5,438,123 | A |   | 8/1995  | Dekeyser et al. |
| 5,567,723 | A |   | 10/1996 | Dekeyser et al. |
| 7,045,512 | B2 | * | 5/2006  | Chee et al. .................. 514/150 |

FOREIGN PATENT DOCUMENTS

WO    WO 9310083         5/1993
WO    WO 2005005376 A2   1/2005

OTHER PUBLICATIONS

Renato C. de Oliviera and Pedro M.O.J. Neves: "Biological Control: Compatibility of Beauveria Bassiana with Acaricides" appearing in Neotropical Entomology, vol. 33, pp. 353-358 (2004).

* cited by examiner

*Primary Examiner*—Golam M. M. Shameem
(74) *Attorney, Agent, or Firm*—Daniel Reitenbach

(57) ABSTRACT

A miticidal triazolidine derivative of the formula

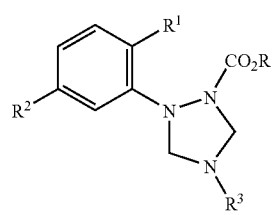

wherein R is $C_1$-$C_6$ alkyl, $C_3$-$C_6$ cycloalkyl, or $C_1$-$C_6$ haloalkyl; $R_1$ is hydrogen, $C_1$-$C_6$ alkoxy, halogen, phenyl or $C_1$-$C_6$ alkyl; $R_2$ is hydrogen, phenyl, thienyl, pyridyl, or thiazolyl, unsubstituted or substituted by one or more substituents selected from $C_1$-$C_4$ alkoxy, $C_1$-$C_4$ alkyl, halogen, and $C_1$-$C_4$ haloalkyl; and $R_3$ is $C_1$-$C_6$ alkyl or benzyl, wherein the alkyl groups can be linear or branched.

18 Claims, No Drawings

MITICIDAL TRIAZOLIDINE DERIVATIVES

FIELD OF THE INVENTION

This invention relates to miticidal triazolidine derivatives. This invention also relates to miticidal compositions comprising the triazolidine derivatives, and to methods of controlling mites, particularly phytophagous mites, using such compounds or compositions.

BACKGROUND OF THE INVENTION

The devastation caused by mites represent a serious economic threat to commercially important food, fiber and ornamental plants. For this reason the development of new and effective miticides represents an ongoing scientific activity.

It is a purpose of this invention to provide novel triazolidine derivatives which are useful as miticides.

SUMMARY OF THE INVENTION

This invention relates to a triazolidine compound of the formula

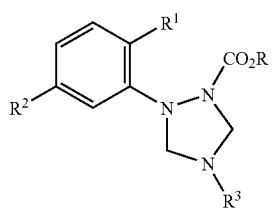

(I)

wherein R is $C_1$-$C_6$ alkyl, $C_3$-$C_6$ cycloalkyl, or $C_1$-$C_6$ haloalkyl; $R_1$ is hydrogen, $C_1$-$C_6$ alkoxy, halogen, phenyl or $C_1$-$C_6$ alkyl; $R_2$ is hydrogen, phenyl, thienyl, pyridyl, or thiazolyl, unsubstituted or substituted by one or more substituents selected from $C_1$-$C_4$ alkoxy, $C_1$-$C_4$ alkyl, halogen, and $C_1$-$C_4$ haloalkyl; and $R_3$ is $C_1$-$C_6$ alkyl or benzyl, wherein the alkyl groups can be linear or branched.

The present invention also relates to a miticidal composition comprising: a) an effective amount of a miticidal compound of formula I; and b) a suitable carrier.

The present invention also relates to a method for controlling mites which comprises applying an effective amount of a miticidal compound of formula I to the mites or to the locus to be protected.

DESCRIPTION OF THE INVENTION

This invention preferably relates to a 6-phenyl-pyridazinone compound of the formula

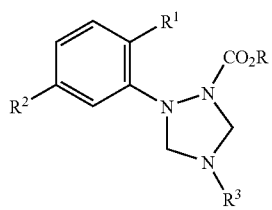

(I)

wherein R is $C_1$-$C_6$ alkyl, $C_3$-$C_6$ cycloalkyl, or $C_1$-$C_6$ haloalkyl; $R_1$ is hydrogen, $C_1$-$C_6$ alkoxy, halogen, phenyl or $C_1$-$C_6$ alkyl; $R_2$ is hydrogen, phenyl, thienyl, pyridyl, or thiazolyl, unsubstituted or substituted by one or more substituents selected from $C_1$-$C_4$ alkoxy, $C_1$-$C_4$ alkyl, halogen, and $C_1$-$C_4$ haloalkyl; and $R_3$ is $C_1$-$C_6$ alkyl or benzyl, wherein the alkyl groups can be linear or branched.

Preferably, R is $C_1$-$C_4$ alkyl or $C_1$-$C_4$ haloalkyl; $R_1$ is hydrogen, $C_1$-$C_4$ alkoxy or $C_1$-$C_4$ alkyl; $R_2$ is hydrogen or phenyl unsubstituted or substituted by one or more substituents selected from $C_1$-$C_4$ alkoxy, $C_1$-$C_4$ alkyl, halogen, and $C_1$-$C_4$ haloalkyl; and $R_3$ is $C_1$-$C_4$ alkyl or benzyl.

More preferably, R is ethyl, propyl, or butyl; $R_1$ is methyl, ethyl, methoxy, or ethoxy; $R_2$ is hydrogen or phenyl; and $R_3$ is methyl, ethyl, propyl, or benzyl.

Most preferably, R is isopropyl, sec-butyl, or t-butyl; $R_1$ is methyl or methoxy; $R_2$ is hydrogen or phenyl unsubstituted; and $R_3$ is methyl, ethyl, or benzyl.

The compounds of the present invention can be prepared according to following reaction scheme:

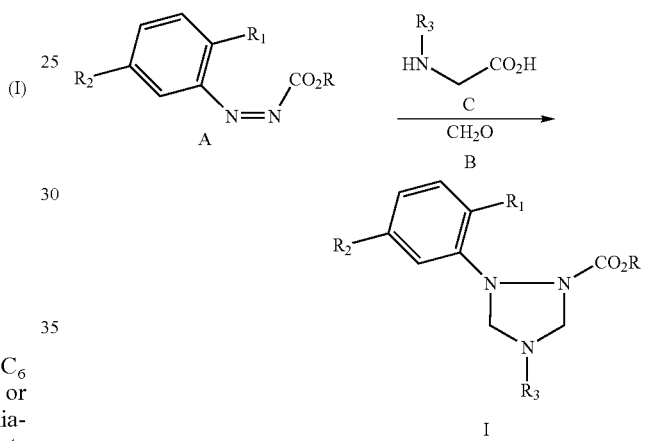

wherein R, $R_1$, $R_2$, and $R_3$ are as described above.

A mixture comprising a diazenecarboxylate of formula A, paraformaldehyde (B) and an amino acid of formula C can be heated at about 100 to about 140° C. in an inert solvent such as toluene, xylene or dioxane, for a period of about one to about four hours. The solvent is then evaporated under reduced pressure, to produce the compound of formula I.

Diazenecarboxylates of formula A are known, see, e.g., U.S. Pat. Nos. 5,567,723 and 5,438,123.

The present invention further relates to a miticidal composition comprising a) an effective amount of a miticidal compound of formula I; and (b) a suitable carrier. Such suitable carriers may be solid or liquid in nature.

The compositions of the present invention can be prepared by formulating one or more compounds of the present invention with a suitable carrier.

Suitable liquid carriers can comprise water, alcohols, ketones, phenols, toluene and xylenes. In such formulations, additives conventionally employed in the art can be utilized, such as one or more surface active agents and/or inert diluents, to facilitate handling and application of the resulting insecticidal composition.

Alternatively, the compounds of this invention can be applied as a liquid or in sprays when utilized in a liquid carrier, such as a solution comprising a compatible solvent such as acetone, benzene, toluene or kerosene, or a dispersion comprising a suitable non-solvent medium such as water.

The compositions of this invention can alternatively comprise solid carriers taking the form of dusts, granules, wettable powders, pastes, aerosols, emulsions, emulsifiable concentrates, and water-soluble solids. For example, the compounds of this invention can be applied as dusts when admixed with or absorbed onto powdered solid carriers, such as mineral silicates, talc, pyrophyllite and clays, together with a surface-active dispersing agent so that a wettable powder is obtained which then is applied directly to the loci to be treated. Alternatively, the powdered solid carrier containing the compound admixed therewith, can be dispersed in water to form a suspension for application in such form.

Granular formulations of the compounds are preferred for field treatment and are suitable for application by broadcasting, side dressing, soil incorporation or seed treatment, and are suitably prepared using a granular or pelletized form of carrier such as granular clays, vermiculite, charcoal or corn cobs. The compound of this invention can be dissolved in a solvent and sprayed onto an inert mineral carrier such as attapulgite granules (10-100 mesh), and the solvent is then evaporated. Such granular compositions can contain from 2-25% by weight of a compound of this invention, based on carrier plus compound, preferably, 3-15%. In addition, the compounds of this invention can also be incorporated into a polymeric carrier such as polyethylene, polypropylene, butadiene-styrene, styrene-acryonitrile resins, polyamides, poly(vinyl acetates), and the like. When encapsulated, the compound of this invention can advantageously be released over an even longer time period, extending its effectiveness further than when used in non-encapsulated form.

Another method of applying the compound of this invention to the loci to be treated is by aerosol treatment, for which the compound can be dissolved in an aerosol carrier which is a liquid under pressure but which is a gas at ordinary temperature (e.g., 20° C.) and atmospheric pressure. Aerosol formulations can also be prepared by first dissolving the compound in a less volatile solvent and then admixing the resulting solution with a highly volatile liquid aerosol carrier.

For treatment of plants (such term including plant parts), the compounds of the invention preferably are applied in aqueous emulsions containing a surface-active dispersing agent which can be non-ionic, cationic or anionic. Suitable surface-active agents are well known in the art, such as those disclosed in U.S. Pat. No. 2,547,724 (columns 3 and 4). The compounds of this invention can be mixed with such surface-active dispersing agents, with or without an organic solvent, as concentrates for the subsequent addition of water, to yield aqueous suspensions of the compounds at desired concentration levels.

In addition, the compounds can be employed with carriers which themselves are pesticidally active, such as insecticides, acaricides, fungicides or bactericides.

It will be understood that the effective amount of a compound in a given formulation will vary depending, e.g., upon the specific chemical composition and formulation of the compound being employed, the method of applying the compound/formulation and the locus of treatment. Generally, however, the effective amount of the compound of this invention can range from about 0.1 to about 95 percent by weight. Spray dilutions can be as low as a few parts per million, while at the opposite extreme, full strength concentrates of the compound can be usefully applied by ultra low volume techniques. When plants constitute the loci of treatment, concentration per unit area can range between about 0.01 and about 50 pounds per acre, with concentrations of between about 0.1 and about 10 pounds per acre preferably being employed for crops such as corn, tobacco, rice and the like.

To combat mites, sprays of the active compounds can be applied to any suitable locus, such as to the mites directly and/or to plants upon which they feed or nest. The compositions of this invention can also be applied to the soil or other medium in which the pests are present.

The specific methods of application of the compounds and compositions of this invention, as well as the selection and concentration of these compounds, will vary depending upon such circumstances as crops to be protected, geographic area, climate, topography, plant tolerance, etc.

Compounds of this invention are useful as acaricides for foliar and/or soil application.

The following examples are provided to illustrate the present invention.

EXAMPLES

Example 1

Preparation of 1-methylethyl 2-(4-methoxy-[1,1'-biphenyl]-3-yl)-4-methyl-1,2,4-triazolidine-1-carboxylate (Compound 1)

To a mixture of 300 mg (1 mmol) 1-methylethyl 2-(4-methoxy-[1,1'-biphenyl]-3-yl)diazenecarboxylate, 180 mg (5 mmol) paraformaldehyde, and 180 mg (1 mmol) glycine was added 10 mL of toluene and the resulting solution was stirred and heated to 120 degrees (F.?) for one hour. After cooling to room temperature, the solvent was removed under reduced pressure (units?) to produce _mg of 1-methylethyl 2-(4-methoxy-[1,1'-biphenyl]-3-yl)-4-methyl-1,2,4-triazolidine-1-carboxylate (in what form, powder, oil, liquid?) as confirmed by NMR.

Compounds 2-6 in Table 1 below were prepared using the same process as described in Example 1 except for a different starting diazenecarboxylate. Each of the compounds so formed is characterized in Table 1 by its NMR data.

TABLE 1

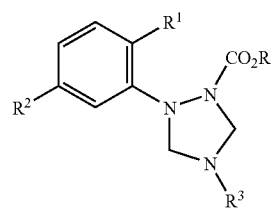

(I)

| No. | R | $R^1$ | $R^2$ | $R^3$ | $^1$NMR data (CDCl3) |
|---|---|---|---|---|---|
| 1 | CH(CH$_3$)$_2$ | OCH$_3$ | C$_6$H$_5$ | CH$_3$ | d (6) 1.2; s (3) 2.5; s (3) 3.9; s (2) 4.3; s (2) 4.4; m (1) 5.0; m (8) 7.0-7.5 |
| 2 | C(CH$_3$)$_3$ | OCH$_3$ | C$_6$H$_5$ | CH$_3$ | t (9) 1.5; s (3) 2.5; s (3) 3.9; s (2) 4.3; s (2) 4.4; m (8) 7.0-7.5 |
| 3 | CH(CH$_3$)$_2$ | OCH$_3$ | C$_6$H$_5$ | CH$_2$C$_6$H$_5$ | d (6) 1.2; s (2) 3.8; s (3) 3.9; s (2) 4.3; s (2) 4.4; m (1) 5.0; m (8) 7.0-7.5 |
| 4 | CH(CH$_3$)$_2$ | OCH$_3$ | C$_6$H$_5$ | CH$_3$ | d (6) 1.2; s (3) 2.4; s (3) 2.5; s (2) 4.0; s (2) 4.5; m (1) 5.0; m (8) 7.0-7.5 |

TABLE 1-continued (I)

![structure]

| No. | R | R¹ | R² | R³ | ¹NMR data (CDCl3) |
|---|---|---|---|---|---|
| 5 | $CH(CH_3)_2$ | $OCH_3$ | $C_6H_5$ | $C_2H_5$ | t (3) 1.1; d (6) 1.2; s (3) 2.4; q (2) 2.6; s (2) 4.1; s (2) 4.5; m (1) 4.9; m (8) 7.2-7.5 |
| 6 | $CH(C_2H_5)$—$(CH_3)$ | $C_6H_5$ | H | $CH_3$ | t (3) 0.9; d (6) 1.3; m (2) 1.6; s (3) 2.3; s (2) 3.5; s (2) 4.3; m (1) 4.8; m (8) 7.1-7.7 |

Example A

Stock Solution Preparation

The remaining examples relate to the miticidal use of the compounds of this invention. In all these examples, a stock solution for the compounds was prepared at 3000 ppm by dissolving each compound to be tested in acetone with 0.67% Tween (v/v), a wetting agent. This stock solution was used in the remaining examples demonstrating the miticidal use of representative compounds of this invention. For each example that follows, this stock solution was used and the specificized dilutions made. All the tests discussed below, which involved treatment with compounds of this invention were always repeated with controls, in which the active compound was not provided, to permit a comparison upon which the percent control was calculated.

Example B

Mite Adulticide Post-Infection, Mite Adulticide Pre-Infection, and Mite Ovicide Tests One day before treatment of cowpea primary leaves with the test solutions, rings of tree tanglefoot were applied to each of two cowpea primary leaves, one from each of two plants in a pot.

For the mite ovicide tests, groups of adult mites (*Tetranychus urticae* Koch) were transferred into the rings one day before treatment and the females were allowed to deposit eggs until one hour before treatment, at which point all the adults were removed. The plants were then sprayed to run off with a 100 ppm solution diluted from the 3000 ppm stock solution.

Nine days following treatment the ovicide rings were examined for unhatched eggs and living immature mites. The percent control was estimated based on the number of unhatched eggs.

For the mite adulticide pre-infection tests, plants were sprayed to run off with a 300 ppm solution diluted from the 3000 ppm stock solution. One day following treatment of the plants with the test solution, groups of approximately 25 adult mites were transferred into the rings. Five days later these rings were examined for live mites remaining on the leaves. The percent control was estimated based on the number of mites surviving on the control plants.

For the mite adulticide post-infection tests, 20 adult twospotted spider mites (*Tetranychus urticae* Koch) were transferred into the rings one day before treatment The plants were then sprayed to run off with a 300 ppm solution diluted from the 3000 ppm stock solution. Five days later these rings were examined for live mites remaining on the leaves. The percent control was estimated based on the number of mites surviving on the control plants.

Results of the mite adulticide pre-infection (MI), mite adulticide post-infection (MIC), and mite ovicide (MIOV) tests are presented below in Table 2.

TABLE 2

| Cmpd. No. | Miticidal Activity Percent Control | | |
|---|---|---|---|
| | MIC | MI | MIOV |
| 1 | — | 100 | 100 |
| 2 | — | 100 | 100 |
| 3 | — | 100 | 0 |
| 4 | 100 | — | 56 |
| 5 | 100 | — | 44 |
| 6 | 90 | — | 12 |

What is claimed is:

1. A triazolidine compound of the formula

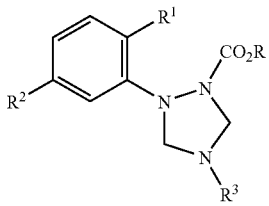

(I)

wherein R is $C_1$-$C_6$ alkyl, $C_3$-$C_6$ cycloalkyl, or $C_1$-$C_6$ haloalkyl; $R_1$ is hydrogen, $C_1$-$C_6$ alkoxy, halogen, phenyl or $C_1$-$C_6$ alkyl; $R_2$ is hydrogen, phenyl, thienyl, pyridyl, or thiazolyl, unsubstituted or substituted by one or more substituents selected from $C_1$-$C_4$ alkoxy, $C_1$-$C_4$ alkyl, halogen, and $C_1$-$C_4$ haloalkyl; and $R_3$ is $C_1$-$C_6$ alkyl or benzyl, wherein the alkyl groups can be linear or branched.

2. A compound as recited in claim 1 wherein R is R is $C_1$-$C_4$ alkyl or $C_1$-$C_4$ haloalkyl.

3. A compound as recited in claim 2 wherein R is ethyl, propyl, or butyl.

4. A compound as recited in claim 3 wherein R is isopropyl, sec-butyl, or t-butyl.

5. A compound as recited in claim 1 wherein $R_1$ is hydrogen, $C_1$-$C_4$ alkoxy or $C_1$-$C_4$ alkyl.

6. A compound as recited in claim 5 wherein $R_1$ is methyl, ethyl, methoxy, or ethoxy.

7. A compound as recited in claim 6 wherein $R_1$ is methyl or methoxy.

8. A compound as recited in claim 1 wherein $R_2$ is hydrogen or phenyl unsubstituted or substituted by one or more substituents selected from $C_1$-$C_4$ alkoxy, $C_1$-$C_4$ alkyl, halogen, and $C_1$-$C_4$ haloalkyl.

9. A compound as recited in claim 8 wherein $R_2$ is hydrogen or phenyl.

10. A compound as recited in claim 9 wherein $R_2$ is hydrogen or phenyl unsubstituted.

11. A compound as recited in claim 1 wherein $R_3$ is $C_1$-$C_4$ alkyl or benzyl.

12. A compound as recited in claim 11 wherein $R_3$ is methyl, ethyl, propyl, or benzyl.

13. A compound as recited in claim 12 wherein $R_3$ is methyl, ethyl, or benzyl.

14. A compound as recited in claim 1 wherein R is $C_1$-$C_4$ alkyl or $C_1$-$C_4$ haloalkyl; $R_1$ is hydrogen, $C_1$-$C_4$ alkoxy or $C_1$-$C_4$ alkyl; $R_2$ is hydrogen or phenyl unsubstituted or substituted by one or more substituents selected from $C_1$-$C_4$ alkoxy, $C_1$-$C_4$ alkyl, halogen, and $C_1$-$C_4$ haloalkyl; and $R_3$ is $C_1$-$C_4$ alkyl or benzyl.

15. A compound as recited in claim 14 wherein R is ethyl, propyl, or butyl; $R_1$ is methyl, ethyl, methoxy, or ethoxy; $R_2$ is hydrogen or phenyl; and $R_3$ is methyl, ethyl, propyl, or benzyl.

16. A compound as recited in claim 15 wherein R is isopropyl, sec-butyl, or t-butyl; $R_1$ is methyl or methoxy; $R_2$ is hydrogen or phenyl unsubstituted; and $R_3$ is methyl, ethyl, or benzyl.

17. A miticidal composition comprising: a) an effective amount of a miticidal compound as recited in claim 1; and b) a suitable carrier.

18. A method for controlling mites which comprises applying an effective amount of a miticidal compound as recited in claim 1 to the locus to be protected.

* * * * *